United States Patent
Borck

(10) Patent No.: US 9,782,255 B2
(45) Date of Patent: Oct. 10, 2017

(54) BIOPROSTHETIC COMPONENTS FOR AN IMPLANT, IN PARTICULAR PARTLY CROSSLINKED BIOLOGICAL HEART VALVES

(71) Applicant: BIOTRONIK AG, Buelach (CH)

(72) Inventor: Alexander Borck, Aurachtal (DE)

(73) Assignee: BIOTRONIK AG, Beulach (CH)

( * ) Notice: Subject to any disclaimer, the term of this patent is extended or adjusted under 35 U.S.C. 154(b) by 0 days.

(21) Appl. No.: 14/033,827

(22) Filed: Sep. 23, 2013

(65) Prior Publication Data

US 2014/0094898 A1    Apr. 3, 2014

Related U.S. Application Data

(60) Provisional application No. 61/708,647, filed on Oct. 2, 2012.

(51) Int. Cl.

| | |
|---|---|
| A61F 2/24 | (2006.01) |
| A61B 17/12 | (2006.01) |
| A61L 27/34 | (2006.01) |
| A61L 27/36 | (2006.01) |
| A61L 31/10 | (2006.01) |

(52) U.S. Cl.
CPC ...... *A61F 2/2412* (2013.01); *A61B 17/12113* (2013.01); *A61L 27/34* (2013.01); *A61L 27/3625* (2013.01); *A61L 31/10* (2013.01); *A61L 2400/18* (2013.01)

(58) Field of Classification Search
CPC . A61L 27/3683; A61L 27/3625; A61F 2/2412
USPC .............................. 623/1.26, 2.13
See application file for complete search history.

(56) References Cited

U.S. PATENT DOCUMENTS

| | | | | |
|---|---|---|---|---|
| 5,549,666 | A * | 8/1996 | Hata et al. ................. | 623/2.13 |
| 6,166,184 | A * | 12/2000 | Hendriks et al. ............ | 530/356 |
| 6,872,226 | B2 * | 3/2005 | Cali ................... | A61F 2/2415 623/2.12 |
| 7,579,381 | B2 * | 8/2009 | Dove ................ | A61L 27/3604 424/422 |
| 8,236,241 | B2 * | 8/2012 | Carpentier et al. .......... | 422/28 |
| 2002/0086977 | A1 | 7/2002 | Lai et al. | |
| 2003/0028247 | A1 | 2/2003 | Cali | |
| 2004/0051213 | A1 * | 3/2004 | Muratoglu ................. | 264/494 |
| 2012/0189588 | A1 * | 7/2012 | Nahas et al. .............. | 424/93.7 |

FOREIGN PATENT DOCUMENTS

| | | |
|---|---|---|
| DE | 2715466 A1 | 10/1977 |
| GB | 1579627 A | 11/1980 |
| WO | 01/28604 A1 | 4/2001 |
| WO | 0128604 A1 | 4/2001 |
| WO | 01/97874 A1 | 12/2001 |
| WO | 0197874 A1 | 12/2001 |
| WO | 2006/066327 A1 | 6/2006 |
| WO | 2006066327 A1 | 6/2006 |

OTHER PUBLICATIONS

K. Schenke-Layland et al., Impact of decellularization of xenogenic tissue on extracellular matrix integrity for tissue engineering of heart valves, Journal of Structural Biology 143 (2003) pp. 201-208.*
Paez et al. "Mechanical Resistance of a New Biomaterial, Ostrich Pericardium, and a New Method of Joining Tissues Combining Suturing and a Biological Adhesive." Journal of Biomedical Materials Research Part B: Applied Biomaterials, Oct. 15, 2004 pp. 9-16.
Paez et al. "Resistance and Stability of a New Method for Bonding Biological Materials Using Sutures and Biological Adhesives" J Biomater Appl. Jan. 2005; 19(3):215-36 XP008166429.
DE2715466A1_MachineTranslation.
Paez et al. "Mechanical Resistance of a New Biomaterial, Ostrich Pericardium, and a New Method of Joining Tissues Combining Suturing and a Biological Adhesive." J Biomed Mater Res Part B: Applied Biomaterials, Oct. 2004, 72B: 9-16, Wily Periodicals.
Paez et al. "Resistance and Stability of a New Method for Bonding Biological Materials Using Sutures and Biological Adhesives" J Biomater Appl. Jan. 2005, 19(3):215-36 XP008166429.
Jones et al. "The quantification of zinc in the mucosal cells of human small intestine using x-ray microanalysis." Scand J Gastroenterol. Suppl. 1981; 70—Abstract XP002718233.
Vasudev et al; The anticalcification effect of polyethylene glycol-immobilized on hexamethylene diisocyanate treated pericardium, Artif Cells Blood Substit Immobil Biotechnol. Jan. 2000, 28(1):79-94. XP-002721519.

* cited by examiner

*Primary Examiner* — Brian Dukert
(74) *Attorney, Agent, or Firm* — Wagenknecht IP Law Group PC

(57) ABSTRACT

Bioprosthetic components based on, or comprising, biological materials for implants, preferably biological heart valves, in particular biological heart valve leaflets, which have only been chemically or thermally stabilized (partly crosslinked) at mechanically stressed points and therefore have zones having different mechanical properties, and to a method for the production thereof.

20 Claims, No Drawings

BIOPROSTHETIC COMPONENTS FOR AN IMPLANT, IN PARTICULAR PARTLY CROSSLINKED BIOLOGICAL HEART VALVES

CROSS REFERENCE TO RELATED APPLICATIONS

This application claims benefit of priority to U.S. provisional patent application Ser. No. 61/708,647 filed Oct. 2, 2012; the entire content of which is herein incorporated by reference in its entirety.

TECHNICAL FIELD

The present invention relates to bioprosthetic components based on, or comprising, biological materials for implants, preferably biological heart valves, in particular biological heart valve leaflets, which have only been chemically or thermally stabilized (partly crosslinked) at mechanically stressed points and therefore have zones having different mechanical properties, and to a method for the production thereof.

BACKGROUND

Bioprosthetic components that are based on a native or possibly modified biological material or that comprise biological materials as a component are also increasingly considered for implants in the prior art. The surface of the biological material that is to be used as a bioprosthetic component for an implant is normally subjected to a stabilizing treatment before use. Common examples for the use of such implants include, for example, various heart valves, such as heart leaflets, aortic valves, mitral valves and pulmonary valves. Further examples for the use of such implants include, for example, venous valves and what are known as "closure devices", such as aneurysm stents, which can be used throughout the blood circulation system, including in the region of the brain, as well as heart leaflets for sealing scarring that may have been caused for example by an operation on the heart, for example the correction of a genetically caused opening between chambers of the heart. The opening between chambers of the heart caused by a gene defect, which may often require treatment as early as childhood, may be an atrioventricular septal defect, an atrial septal defect or a ventricular septal defect for example.

In mammals, the heart is the organ responsible for maintaining an adequate supply by pumping blood throughout the body so that all parts of the body are supplied sufficiently with oxygen and nutrients. The back-flow of blood into the heart is prevented by four valves (heart valves), which are used as an inlet and outlet for each of the two chambers of the heart, which serve as pump chambers of the heart.

Incorrect functioning of one or more of these valves may have serious implications for health. Such incorrect functioning may be caused by deformations from birth or by damage caused by disease. Forms of incorrect functioning include stenosis (a narrowing in the mouth of the open valve) and the back-flow of blood through the closure or through the closed valve, wherein both situations require increased performance of the heart to maintain the corresponding blood flow in the body. In many cases, the only effective solution lies in replacing the incorrectly functioning valve.

The use of artificial heart valves unfortunately requires life-long treatment with anticoagulants for patients, since blood clots may otherwise form on the valve mechanism of the artificial heart valve. Blood clots on the valve mechanism may limit the movability of the parts of the valve aperture, may impair valve function or may detach from the valve mechanism and close the blood vessels behind the valve. In the case of mechanical valves, the closure element rotates in the flow-through opening, but is not moved away from the flow-through opening when the valve opens. This limits the flow of blood, but, more importantly, it disturbs the blood flow patterns. This disturbance of the blood flow is generally considered to be a cause of, or at least a significant contribution to, the observed tendency of mechanical valves to cause blood clotting.

Biological prostheses, for example biological replacement heart valves, that are obtained from natural tissues may be preferred due to specific clinical advantages compared to mechanical devices. For example, in tissue-based prostheses the routine anticoagulation is generally not necessary and, whereas mechanical prostheses may typically fail suddenly, there is conversely generally initially a gradual worsening with tissue-based prostheses, which can last for a period of months or even years and therefore provides an early indication of a possible failure. Besides artificial heart valves, biological heart valves are therefore also used as a replacement for incorrectly functioning heart valves in specific patient groups, for example in which the implantation of artificial heart valves is rejected.

Although the likelihood of blood clotting with biological heart valves is much lower compared to mechanical replacement valves, and patients with biological heart valves therefore generally do not have to be treated with anticoagulants, with the exception of the immediate post-operative period, the known biological heart valves still also require improvement. Biological heart valves can degenerate over time, often as a result of mineralization or calcification of the crosslinked natural tissue, which poses a serious problem in young patients in particular. Although receivers of a biological heart valve therefore do not have to take anticoagulants, such as Marcumar, the service life of biological heart valves is much shorter than that of mechanical valves.

Although any prosthetic valve may fail as a result of mineralization, such as calcification, this problem of gradual prosthesis degeneration is of particular clinical significance in the case of bioprosthetic heart valves obtained from tissue. The pathogenesis of the calcification is not fully known, and, in addition, even today there is still the lack of a sufficiently effective therapy.

Possible causes will be described briefly, without favoring or being tied to a specific theory. For example, with regard to the source of mineralization and of calcification in particular, it has been proven that these start primarily with cell debris, which occurs in tissue matrices of bioprosthetic heart valves, more specifically equally in bioprosthetic heart valves originating from pericardium or aortic root. The calcification of bioprosthetic crosslinked tissue has also been linked to the presence of alkaline phosphatases in cell debris and the possible accumulation thereof within the implanted tissue from the blood. Mineralization could also be caused by the fact that phospholipids in the cell debris sequester calcium and form the nucleation point of apatite (calcium phosphate). It has also bee proposed that sub-units of elastin and fibrillin may be a cause of calcification due to the calcium-binding function of these proteins. Irrespective of its mechanism, mineralization in bioprostheses, and calcification in particular, is considered to be the most common cause of the clinical failure of bioprosthetic heart valves obtained from porcine aortic valves or bovine pericardium.

In the case of human aortic homograft implants, pathological calcification has likewise been observed, although in this case it occurs more slowly than with bioprosthetic heart valves, but affects both the valve tissue and also the adjacent aortic wall. Pathological calcification ultimately leads to failure of the valve, for example in the form of stenosis and/or regeneration, and requires re-implantation. Since bioprosthetic heart valves and also homograft heart valves are subject to calcification, the clinical use thereof is now limited, in spite of some solution approaches to reduce or prevent mineralization or calcification.

A number of methods for reducing mineralization and calcification in bioprosthetic heart valves to the greatest possible extent or for eliminating these processes have been applied in the prior art. In these methods, the bioprosthetic heart valves are normally treated with various substances before implantation. Suitable substances that have been described include sulfated aliphatic alcohols, phosphate esters, amino acids, diphosphonates, derivatives of carboxylic acids and various surfactants. Another method uses amino oleic acid (AOA) as a means for alleviating calcification in bioprosthetic heart valves made of porcine aortic root tissue. Effective prevention of mineralization of the aortic wall could not previously be achieved by application of these methods however, and a successful solution to the problem of the occurrence of mineralization after implantation is still yet to be developed.

Furthermore, bioprostheses made of animal tissue, for example porcine heart valves, trigger immunogenic and inflammatory reactions of varying severity in receivers. It is therefore attempted generally, and in the case of the present invention too, to prevent an immunological rejection by means of chemical treatment of the animal tissue. The current method of glutaraldehyde fixing can indeed considerably mask the antigenicity of an implanted porcine valve tissue, but cannot overcome it completely. Even porcine heart valves may therefore still lead, after glutaraldehyde fixing, to a slight to severe inflammatory reaction, which can be attributed in part to the cytotoxic nature of glutaraldehyde, and in more severe cases the foreign tissue may even cause a chronic inflammatory reaction.

Reference is made to patent publications U.S. Pat. No. 6,166,184 (Methods for making bioprosthetic devices) and U.S. Pat. No. 6,509,145 (Process for reducing mineralization of tissue used in transplantation), and to published US patent applications U.S. Pat. No. 7,078,163, US 2003/0118981 A1 (Process for reducing mineralization of tissue used in transplantation), WO 2005/011764, US 2005/0020506 A1 (Crosslinked compositions comprising collagen and demineralized bone matrix, methods of making and methods of use) as exemplary methods for treating tissues before transplantation, the aforesaid documents describing methods for treating biological tissue before implantation.

Previously, the biological heart valves, for example the heart valve leaflets, were also decellularized. "Decellularization" is understood to mean a method for removing cells and cell debris from tissue and tissue structures. This decellurization is generally applied in the case of bioprosthetic heart valves produced from porcine aortic valves or bovine pericardium.

US 2005/0266390 A1 thus describes a method for decellurization of mammalian tissue for use in transplant medicine and tissue engineering. In this method an ionic detergent and a non-ionic detergent are applied simultaneously to mammalian tissue over a relatively long period of time, which may last for more than five days. In this case, SDS for example is used as an ionic detergent and Triton X-100 is used as a non-ionic detergent. A considerable rinsing step follows, which likewise may last for more than five days. This extraction with subsequent rinsing is supposed to deliver a tissue with stress-strain curves and DSC data similar to that of fresh, unprocessed tissues. US 2005/0266390 A1 also discloses the fact that the processed tissue is free from cells for the most part and that the underlying structure remains substantially intact and demonstrates much improved behavior with regard to inflammatory reactions relative to fresh tissue, even without glutaraldehyde fixing, as well as a much lower level of calcification in situ based on glutaraldehyde-fixed tissue. For example, the method can be used for the decellurization of porcine heart valve leaflets and porcine heart wall tissue before use in transplantation.

WO 2005/118014 also describes a method for decellurization for tissue that is to be used as a bioprosthetic replacement in transplantations. The method of WO 2005/118014 concerns the treatment of tissue that still contains cell membranes and is cut from an animal for the production of a tissue-based implantable bioprosthesis. In this method the cut tissue is contacted simultaneously with two different detergents, wherein one is an ionic detergent that can destroy cell membranes, and the other is a detergent having a neutral net charge.

However, decellurization leads to a material that has inadequate mechanical properties. So as to improve the mechanical properties of the material, the entire material is chemically crosslinked in the prior art and is thus mechanically improved, that is to say as a result of treatment of the entire surface and of the underlying layers. Chemical crosslinking involves risks, however. Groups that have not abreacted have to be removed, which is costly, so as to ensure a sufficient biocompatibility of the material. Examples of these efforts made in the prior art to again remove crosslinking reagents such as glutaraldehyde include the "ThermaFix" method (Edwards) or the "AOA Tissue Treatment" method (Medtronic). In the case of "AOA Tissue Treatment" for example, this involves the above-mentioned treatment of the tissue using amino oleic acid (AOA).

The "ThermaFix" process involves a treatment of the tissue that is effective against lime deposits. Glutaraldehyde fixing is merely the first step of the tissue treatment in this instance (Southern L J, et al. Glutaraldehyde—indeed crosslinks: a study of model compounds and commercial bioprosthetic valves. J Heart Valve Dis 2000; 9 (2):241-8). Glutaraldehyde fixing assists tissue conversion and sterility and improves biocompatibility and structural stability. If, with the tissue treatments in the prior art, calcium deposit sites such as phospholipids and unstable glutaraldehyde radical molecules are merely chemically bonded, the effect against lime deposition may decrease over time. Compared to chemical bonding (fixing) alone, a further improvement can be achieved by subsequent extraction. With the enhanced "ThermaFix" tissue method, the calcium deposit sites such as phospholipids and unstable glutaraldehyde radical molecules are therefore additionally extracted.

The prior art methods have the disadvantage that the entire surface of the biological material is chemically altered, possibly including the underlying layers in part or completely, although in practice tears and a failure of the structure occur predominantly at the edges of the biological material. In addition, the biological material is made stiffer on the whole as a result of the treatment of the entire heart valve, and this leads to a homogeneous material over the entire heart valve. This contradicts the locally different requirements of the heart valve. For example, the edge regions are subject to different stresses at the stitching points compared to at the edge regions in the lumen, wherein the requirements in the central region of the heart valve are in turn quite different.

In the prior art there is therefore still a considerable need, for implants, to improve the properties of bioprosthetic components that are based on, or comprise, biological materials, particularly in view of mechanical stability, service life and biocompatibility for example. In this case, there is a specific need to improve the properties of biological heart valves inter alia, in particular of biological heart valve leaflets, for use thereof as implants.

There is thus still a considerable demand for an improved bioprosthetic or biological heart valve replacement having good hemodynamic performance, a long service life, and/or improved biocompatibility, for example with a sufficient reduction in the risk of the induction of blood clotting so that the use of anticoagulants after implantation can be omitted, and/or a minimal risk of mineralization and/or calcification. There is also a need for other improved, permanent and non-immunogenic or only slightly immunogenic bioprosthetic tissues that are also compatible for patients in terms of healing and growth.

There is accordingly also a need for the provision of bioprosthetic (biological) heart valves and/or other implants (bioprosthetic materials), obtained from (homogeneous or xenogeneic) tissues, having improved biocompatibility, for example those that resist pathological calcification in the long term in vivo, and wherein the bioprosthetic (biological) implants, in particular heart valves, preferably also have improved long-term mechanical stability or ability to withstand continuous stressing. There is also a need for methods with which bioprosthetic (homogeneous or xenogeneic) tissue (or implants based thereon) having improved biocompatibility, for example that having reduced inflammatory and immune response, can be provided and with which bioprosthetic (homogeneous or xenogeneic) tissue in particular (or implants based thereon) having improved long-term mechanical stability or ability to withstand continuous stressing can also be produced.

DETAILED DESCRIPTION

The object of the present invention is therefore to provide bioprosthetic components for implants, preferably bioprosthetic (biological) heart valves, in particular bioprosthetic (biological) heart valve leaflets, and possibly also other implants obtained from (homogeneous or xenogeneic) tissue, having improved biocompatibility and in particular have long-term mechanical stability or ability to withstand continuous stressing. More specifically, in a preferred variant the object of the invention is to provide bioprosthetic (biological) heart valves, in particular bioprosthetic (biological) heart valve leaflets, having improved biocompatibility, for example those that resist pathological calcification in the long term in vivo to the greatest possible extent and in particular have improved long-term mechanical stability or ability to withstand continuous stressing.

In another variant the object of the invention is to also provide other implants (bioprosthetic materials) that are obtained from (homogeneous or xenogeneic) tissues and have improved biocompatibility, for example those that resist pathological calcification in the long term in vivo to the greatest possible extent, and in particular those that have improved long-term mechanical stability or ability to withstand stressing.

A further object also lies in specifying methods with which bioprosthetic (biological) heart valves having the above-mentioned improved properties, in particular bioprosthetic (biological) heart valve leaflets, and possibly also other implants (bioprosthetic materials), obtained from (homogeneous or xenogeneic) tissues, having improved biocompatibility and in particular having long-term mechanical stability or ability to withstand continuous stressing can be produced.

The object is achieved, as will be described in greater detail hereinafter, in that a merely (area-based) partial stabilizing treatment of the selected biological tissue is carried out, wherein, as a result of the partial treatment, a mechanical stability is preferably produced precisely at those points where failure of the material may also occur in the event of continuous stressing. At the same time the scope of the modification, for example caused by chemical substances or thermally, in the selected biological tissue is limited locally. In accordance with the present invention, the majority of the surface of the selected biological tissue remains natively untreated or at least unaffected by the (additional) stabilizing treatment and therefore is also more biocompatible than the fully treated biological tissue. In particular, the present invention can be applied, in a non-limiting manner however, with the use of mammalian tissues, for example porcine aortic valves or bovine pericardium, for the production of bioprosthetic (biological) heart valves, for example preferably for the production of bioprosthetic (biological) heart valve leaflets.

The present invention will be described in greater detail further below on the basis of the example of biological heart valves, in particular biological heart valve leaflets, although it is not restricted thereto and can also generally be applied similarly to other biological or bioprosthetic tissue and thus also play a significant role in these other bioprostheses. Besides the heart valves already discussed, such bioprostheses may also be, for example, vessel prostheses, venous transplants, or urinary bladders, pericardia, left-ventricular aids and the like, which are obtained with use of natural, for example homogeneous or xenogeneic, tissue.

In its broadest embodiment, the present invention therefore generally concerns bioprosthetic components for implants, preferably bioprosthetic (biological) heart valves, in particular bioprosthetic (biological) heart valve leaflets, and possibly also other implants obtained from (homogeneous or xenogeneic) tissues, having improved biocompatibility and in particular having long-term mechanical stability or ability to withstand continuous stressing. The invention is applicable to all types of implants in which tissue is used, for example grafts such as closure devices, generally in valve systems such as venous valves or heart valves, for example heart leaflets, mitral valves, aortic valves and pulmonary valves. In what are known as "closure devices", the present invention can be applied to implants or biological components thereof, for example in the region of the brain (in brain aneurysms) or in blood vessel systems, in particular the heart, in the event of aneurysms occurring there. They can also be applied to heart leaflets to seal a scar, wherein the scarring may have been produced for example by an operation or a treatment of a genetically induced opening between chambers of the heart. Examples of such an opening caused by a gene defect, which often require treatment as early as childhood, include atrioventricular septal defects, atrial septal defects and ventricular septal defects.

The invention therefore generally relates to a bioprosthetic component for an implant, based on a native or possibly already modified biological material, wherein, due to a separate stability-increasing treatment of just part of the surface, the surface of the biological material has one or more zones having an increased mechanical stability compared to the mechanical stability before the stability-increasing treatment, and wherein, in each case based on the total surface of the bioprosthetic component as 100%, the zones having increased mechanical stability account for a proportion of ≤40% of the surface and the properties of the remaining zones having a proportion of ≥60% of the surface are substantially unaltered before and after the stability-increasing treatment.

It is preferable if ≥0.5%, preferably ≥2%, more preferably ≥5% and particularly preferably ≥10% of the surface of the bioprosthetic component is modified by the (area-defined) surface treatment. Accordingly, the proportion of the surface of the bioprosthetic component substantially unaltered before and after the stability-increasing treatment is then ≤99.5%, preferably ≤98%, more preferably ≤95%, and particularly preferably ≤90% of the surface.

The bioprosthetic component according to the invention for an implant may be intended in this case for an implant that is selected from the group consisting of (1) closure devices, preferably aneurysm stents for the entire blood circulation system, including the blood circulation system in the region of the brain; (2) valve systems, preferably biological heart valves and venous valves, particularly preferably biological heart valves selected from the group consisting of heart valve leaflets, mitral heart valves, aortic heart valves and pulmonary heart valves; and (3) tissue leaflets for sealing organ scarring, preferably heart leaflets for sealing scarring in the heart, particularly preferably heart leaflets for sealing scarring in the heart in the case of an atrioventricular septal defect, an atrial septal defect or ventricular septal defect.

Such a bioprosthetic component according to the invention for an implant can be further characterized in that the surface of the bioprosthetic component has one or more zones having increased mechanical stability, wherein the increased mechanical stability is based on a separate stability-increasing treatment of the surface of these zones, which is a stability-increasing chemical and/or thermal treatment. Examples of such separate stability-increasing treatments of the surface or of the aforesaid zones of the surface will be described in greater detail further below in conjunction with heart valves, in particular heart leaflets.

In advantageous bioprosthetic components according to the invention for implants, the surface of the bioprosthetic component has one or more zones having increased mechanical stability, wherein such a zone forms the basis of an increased ability to withstand continuous mechanical stressing with appropriate use of the bioprosthetic component, and wherein this zone is preferably at least an edge and/or stitching edge and/or stitching region and/or other fixing region of the bioprosthetic component or a combination of these zones, and wherein this zone is particularly preferably at least one stitching edge or stitching region of the bioprosthetic component.

As already stated, in a bioprosthetic component according to the invention for an implant, it is expedient if only part of the surface of the biological material is altered or stabilized by a separate additional stability-increasing treatment. An expedient variant of the invention therefore concerns a bioprosthetic component for an implant, said bioprosthetic component being characterized in that the zones therein with increased mechanical stability, in each case based on the total surface of the bioprosthetic component as 100%, account for a proportion of ≤30%, in particular of ≤20%, preferably a proportion of from 5 to 20%, particularly preferably a proportion of from 10 to 20%, of the surface. A further expedient variant of the invention may therefore also be a bioprosthetic component for an implant, said bioprosthetic component being characterized in that the properties of the remaining zones therein, that is to say of the zones without a separate additional stability-increasing treatment, having a proportion of ≥70%, in particular ≥80%, preferably of from 95 to 80%, particularly preferably of from 90 to 80%, of the surface of the heart valve leaflet, in each case based on the total surface of the bioprosthetic component as 100%, are substantially unaltered before and after the stability-increasing treatment.

The invention will be described further hereinafter, initially generally for bioprosthetic components for implants. Further details concerning the following general embodiments of the invention for bioprosthetic components can be found in the embodiments of the invention described in greater detail further below on the basis of the example of heart valves, in particular on the basis of the example of heart valve leaflets, and can be applied similarly or in a manner adapted by a person skilled in the art as desired.

In a further variant of the invention, the biological material in the bioprosthetic components for an implant, based on a native or possibly already modified biological material, may be a biological material already modified by chemical pre-treatment, preferably a biological material modified by decellularization.

A preferred bioprosthetic component according to the invention for an implant is characterized in that the implant is a biological heart valve, in particular a heart valve leaflet, based on a native or possibly already modified biological material. In this case, a biological heart valve, in particular a heart valve leaflet, based on a native or possibly already modified biological material is very preferred, wherein the biological material is a biological material already modified by chemical pre-treatment, particularly preferably a biological material modified by decellularization.

Such a bioprosthetic component for an implant can be further characterized in that the implant is a biological heart valve, in particular a heart valve leaflet, based on biological material. Such a bioprosthetic component according to the invention for an implant, rather generally but preferably a biological heart valve, in particular a heart valve leaflet, is based on a biological material, wherein the biological material already modified by chemical pre-treatment, preferably modified by decellularization, is a biological material modified and/or decellularized by treatment with a glutaraldehyde solution, preferably by treatment with a 0.3 to 1.0% by weight glutaraldehyde solution, particularly preferably with a 0.6% by weight glutaraldehyde solution, based on a phosphate-buffered isotonic sodium chloride solution having a pH of from 7.2 to 7.5. More specifically, the glutaraldehyde solution or the concentration range thereof can thus be characterized, for example, as a 0.3 to 1% by weight phosphate-buffered isotonic sodium chloride solution (PBS 50 mM phosphate); a preferred pH value is the pH of 7.38.

One embodiment of the invention concerns a bioprosthetic component for an implant, wherein the bioprosthetic component, preferably a biological heart valve, in particular a heart valve leaflet, is based on a biological material, wherein the surface of the bioprosthetic component, preferably of the biological heart valve, in particular of the heart valve leaflet, has one or more zones having increased mechanical stability, wherein the increased mechanical stability is based on a separate stability-increasing treatment of the surface of these zones with a 0.5 to 25% by weight glutaraldehyde solution in acetone, and is preferably based on a separate stability-increasing treatment with a 0.6 to 2% by weight glutaraldehyde solution in acetone.

A further embodiment of the invention concerns a bioprosthetic component for an implant, wherein the bioprosthetic component, preferably a biological heart valve, in particular a heart valve leaflet, is based on a biological material, and wherein the surface of the bioprosthetic component, preferably of the biological heart valve, in particular of the heart valve leaflet, has one or more zones having increased mechanical stability, in which the increased mechanical stability is based on a polymer coating that is formed in situ from a) an isocyanate component, preferably with HMDI (hexamethyldiisocyanate) as the isocyanate component; and b) a further component selected from b1) a polyol component, preferably with a saccharide or polysaccharide as the polyol component, if desired with addition of DABCO (1,4-diazabicyclo[2.2.2]octane) as an alkaline catalyst, or b2) a polyamine component, preferably with polyethyleneimine as the polyamine component.

In another embodiment the invention concerns a bioprosthetic component for an implant, characterized in that the bioprosthetic component, preferably a biological heart valve, in particular a heart valve leaflet, is based on a biological material, and wherein the surface of the bioprosthetic component, preferably of the biological heart valve, in particular of the heart valve leaflet, has one or more zones having increased mechanical stability, wherein the increased mechanical stability is based on a separate stability-increasing treatment of the surface of these zones with divinyl sulfone and a mixture of a branched polyethylene amine and divinyl sulfone.

In one embodiment the invention further relates to a bioprosthetic component for an implant, characterized in that the bioprosthetic component, preferably a biological heart valve, in particular a heart valve leaflet, is based on a biological material, and wherein the surface of the bioprosthetic component, preferably of the biological heart valve, in particular of the heart valve leaflet, has one or more zones having increased mechanical stability, wherein the increased mechanical stability is based on a separate stability-increasing treatment of the surface of these zones by shaping and by a short-term thermal treatment, preferably with shaping by cutting with a laser and short-term thermal heating of the cut region or by shaping by punching and subsequent short-term intense heating of the punched region.

The bioprosthetic component according to the invention for an implant can be provided very advantageously in the region with a stitching. The edge region can be stitched, in a manner that is known per se to be standard to a person skilled in the art, using any yarn known per se in the prior art and suitable for the stitching of biological material. Various sewing techniques are known from the textiles industry and can be used. A monofilament or a multifilament can be used as suture material. For example, TEVDEK II® by Deknatel or PROFILEN® by Lenzing are well suited. Pure Teflon has proven to be particularly expedient due to its low coefficient of friction during the sewing process.

Bioprosthetic components for an implant according to the embodiments of the invention are preferably further characterized in that the bioprosthetic component, preferably a biological heart valve, in particular a heart valve leaflet, is based on a biological material, and wherein the surface of the bioprosthetic component, preferably of the biological heart valve, in particular of the heart valve leaflet, has one or more zones having increased mechanical stability, wherein such a zone has the following material property and/or tear resistance: SRS of from 30 to 450 N/mm², preferably of from 50 to 300 N/mm², more preferably of from 100 to 200 N/mm², particularly preferably of from 150 to 200 N/mm². The suture retention strength of sample material can be established in 0.9% physiological saline solution at 37° C. with the aid of a test machine that is able to maintain a continuous test speed (mm/min) and to establish the stress-elongation curve. Details regarding the determination of the suture retention strength of sample material are described in greater detail further below on the basis of the example of heart valves.

The bioprosthetic components and implants according to the invention are characterized in part by their production method, as has been described above and as will also be described hereinafter. It is clear to a person skilled in the art that, within the context of the invention, it is irrelevant whether the characterizing production method has actually been applied for the respective component/the respective implant, and it is merely important that the component according to the invention/the implant according to the invention is provided with features and properties that can also be achieved by means of the methods used for characterization purposes. Accordingly, the invention also relates to objects that have not actually been produced using the methods described for characterization purposes, but which could have been produced thereby.

Lastly, the invention also relates to a method for producing a bioprosthetic component for an implant, preferably a biological heart valve, in particular a heart valve leaflet, as defined according to the present invention, wherein the bioprosthetic component for an implant, preferably the biological heart valve, in particular the heart valve leaflet, is based on a native or possibly already modified biological material, and wherein the surface of the bioprosthetic component for an implant, preferably of the biological heart valve, in particular of the heart valve leaflet, has one or more zones having an increased mechanical stability, wherein the method according to the invention is characterized in that only part of the surface of the bioprosthetic component for an implant, preferably of the biological heart valve, in particular of the heart valve leaflet, is subjected to a separate stability-increasing treatment, preferably a separate stability-increasing chemical and/or thermal treatment, so as to produce one or more zones having an increased mechanical stability compared to the mechanical stability before the stability-increasing treatment, and wherein, in each case based on the total surface of the bioprosthetic component for an implant, or preferably of the biological heart valve, or in particular of the heart valve leaflet, as 100%, the zones with increased mechanical stability are formed by a maximum proportion of up to 40% of the surface and the properties of the remaining zones having a proportion of at least 60% of the surface remain substantially unaltered by the stability-increasing treatment.

To solve the particular object on which it is based, the invention specifically provides the solution of bioprosthetic (biological) heart valves, in particular bioprosthetic (biological) heart valve leaflets, having improved biocompatibility, for example those that resist pathological calcification in the long term in vivo to the greatest possible extent, and in particular have improved long-term mechanical stability or ability to withstand continuous stressing.

The invention will now be explained in greater detail on the basis of the example of biological heart valves. In this regard, one embodiment of the invention concerns a biological heart valve, in particular a heart valve leaflet, based on a native or possibly already modified biological material, of which the surface, due to a separate stability-increasing treatment of just part of the surface, has one or more zones having an increased mechanical stability compared to the mechanical stability before the stability-increasing treatment, and wherein, in each case based on the total surface of the biological heart valve, or in particular of the heart valve leaflet, as 100%, the zones with increased mechanical stability account for a maximum proportion of ≤40% of the surface and the properties of the remaining zones having a proportion of ≥60% of the surface are substantially unaltered before and after the stability-increasing treatment.

The invention can be applied to all types of biological heart valves. Such biological heart valves can be obtained from pigs or from other animal or human tissues or with use of other animal or human tissues. In the case of these biological heart valves, the valve tissue may consist of human (homograft) or animal (xenograft) tissue. In particular, porcine aortic valves or bovine pericardium can be used as a basis for the biological heart valves, in particular the biological heart valve leaflets. Animal and human donor valves have to be preserved after removal for subsequent implantation. Cryopreservation in liquid nitrogen has proven to be the most effective method. Alternatives include preparation in an antibiotic solution at 4° C., X-ray irradiation and dry-freezing As a result of the invention, a biological replacement for each of the total of four natural heart valves can thus be provided. The natural heart valves function as valve mechanisms in the heart and prevent a back-flow of blood in the incorrect direction. They are formed of leaflet-like or pocket-like structures protruding into the clearance, which are duplications of the endocardium reinforced inwardly by connective tissue. Each half of the heart has an atrioventricular valve and a semilunar valve. The atrioventricular valves are located between the respective atrium and ventricle and are referred to as the bicuspid valve or mitral valve (left-hand side) and the tricuspid valve (right-hand side). The semilunar valves are each arranged between the respective ventricle and outflow vessel and are referred to as the pulmonary valve (right-hand side) and aortic valve (left-hand side).

Natural heart valves use wings made of thin, flexible tissue as a closure element. The wings move slightly from the opening as soon as blood starts to flow through the heart valve, so that the flow of blood through the opened heart valve is not prevented by the wings. The biological heart valves according to the invention function analogously and thus enable a relatively unrestricted flow-through opening when the heart valve is opened.

The heart valves that are characterized by leaflet-like flaps (Cuspes) are referred to as atrioventricular valves. Atrioventricular valves are found on either side of the heart in mammals, between the atrium (Atrium) and the ventricle (Ventriculus), and may therefore also be referred to as AV valves (Valvae atrioventriclares). The atrioventricular valve on the right-hand side of the heart consists in mammals of three leaflets and is therefore referred to as the tricuspid valve. The atrioventricular valve on the left-hand side of the heart has just two leaflets in mammals and is therefore referred to as the bicuspid valve.

The leaflets are fastened at their base to the skeleton of the heart and at their free edge via Chordae tendineae via the papillary muscles.

Histologically, atrioventricular valves consist of four layers. The atrial layer (Lamina atrialis) facing the atrium of the heart consists of a layer of endothelial cells, which are derived from the endocardium. They are arranged on a thin layer of connective tissue fibers and smooth muscle cells. The sponge layer (Lamina spongiosa) made of loose connective tissue containing collagen fibers, fibroblasts, elastic fibers and anitschkow cells, which are embedded in a base substance made of proteoglycans, is arranged beneath the Atrialis. The connective tissue layer (Lamina fibrosa) consists of dense connective tissue and continues at the base of the valve into the Anuli fibrosi of the skeleton of the heart and at the free edges into the surface of the heart strings. The ventricular layer (Lamina ventriclaris) facing the ventricle consists of endothelial cells and connective tissue, similarly to the Atrialis, although in this case no smooth muscle cells are incorporated.

The heart valves that are characterized by half-moon-shaped pockets arranged in a sponson-like manner are referred to as semilunar valves (Valvulae semilunares). Semilunar valves are located at the two outflow paths of the ventricles of the heart in mammals. The semilunar valve of the aorta is referred to as the aortic valve (Valva aortae), which denotes the Truncus pulmonalis pulmonary valve (Valva trunci pulmonalis). Semilunar valves consist of a duplication of the inner skin of the heart (endocardium). The free edges may have nodule-like thickenings, which are referred to as Noduli valvarum semilunarium and improve closure of the valve.

Considerable advantages compared to the prior art in bioprosthetic materials, in particular in biological heart valves and specifically heart valve leaflets, are achieved by the invention. The bioprosthetic or biological material according to the present invention is thus only stabilized mechanically in part. The separate stability-increasing treatment of the (selected) part of the surface of bioprosthetic or biological materials, in particular of bioprosthetic or biological heart valves, and specifically of bioprosthetic or biological heart valve leaflets, preferably lies in the fact that crosslinking and mechanical stabilization are achieved by chemical or thermal treatment. In one embodiment, the invention accordingly relates to a biological heart valve, in particular a biological heart valve leaflet, based on biological material, of which the surface has one or more zones having increased mechanical stability, wherein the increased mechanical stability is based on a separate, stability-increasing treatment of the surface of these zones, which is a separate stability-increasing chemical and/or thermal treatment In accordance with the invention special attention is paid to the mechanical stabilization of edge regions, in particular of edge regions subject to continuous mechanical stress. These edge regions undergo mechanical stabilization as a result of crosslinking due to the separate stability-increasing treatment of just this selected part of the surface. Besides the border regions such as edges, the stitching region of the biological material may also be stabilized in addition. The mechanical requirements in the stitching region are quite different compared to in the other regions of the biological material, in particular of a biological heart valve and specifically of a heart valve leaflet. The stitching region of a biological heart valve according to the invention, in particular of a biological heart valve leaflet according to the invention, is characterized in that a yarn does not function through the tissue in the event of tensile loading and therefore rips out the tissue. As a result of the solution according to the invention, bioprosthetic or biological materials, in particular bioprosthetic or biological heart valves and specifically bioprosthetic or biological heart valve leaflets, that have modified material properties according to location are available. This gradient of the locally varying material properties has a direct effect on tear resistance and/or other material characteristics.

The suture retention strength of sample material can be established in 0.9% physiological saline solution at 37° C. with the aid of a test machine that is able to maintain a continuous test speed of approximately 10-100 mm/min and to establish the stress-elongation curve. Sample material is positioned centrally in a clamping jaw and fixed at one end for this purpose. A loop made of surgical suture material is then attached two millimeters from the edge of the sample (rectangular sample geometry) and is placed and fastened in a second, upper clamping jaw. Once the sample has been fixed, the measurement to establish the maximum force and the maximum elongation is taken. The suture retention strength (SRS) in $N/mm^2$ is established from the maximum force and the thickness of both the sample material and suture material. The SRS for fixed biological pericardium for example, for use for heart valves, lies in a range of >100 $N/mm^2$. Partly fixed regions of the valve leaflet made of bioprosthetic or biological materials, and in this case biological heart valves specifically, in particular a biological heart valve leaflet, based on biological material of which the surface has one or more zones having increased mechanical stability, meet at least these requirements of the SRS in terms of the ability of the material to withstand stressing.

In one embodiment the present invention therefore relates to bioprosthetic or biological materials, and specifically a biological heart valve, in particular a biological heart valve leaflet, based on biological material, of which the surface has one or more zones having increased mechanical stability, wherein such a zone forms the basis of an increased ability to withstand continuous mechanical stressing with appropriate use of the heart valve, in particular of the heart valve leaflet, and is preferably at least an edge and/or stitching edge and/or stitching region and/or other fixing region of the heart valve leaflet or a combination thereof, and is particularly preferably at least one stitching edge or stitching region of the heart valve leaflet.

The proportion of the surface of the bioprosthetic or biological material, and specifically of the biological heart valve and in particular of the biological heart valve leaflet, which in accordance with the present invention is only partly stabilized mechanically by the separate stability-increasing treatment of the selected part of the surface, can vary within specific limits, depending on the requirements, for example depending on the clinical requirements. The present invention therefore preferably relates to bioprosthetic or biological materials, and specifically a biological heart valve, in particular a biological heart valve leaflet, based on biological material that is characterized in that the zones with increased mechanical stability, in each case based on the total surface of the biological heart valve, or in particular of the heart valve leaflet, as 100%, account for a proportion of up to ≤30%, in particular of ≤20%, preferably of from 5 to 20%, particularly preferably of from 10 to 20%, of the surface. In a preferred variant of this embodiment of the invention, a bioprosthetic or biological material is provided, specifically a biological heart valve, in particular a biological heart valve leaflet, based on biological material that is characterized in that the properties of the remaining zones therein having a proportion of ≥70%, in particular of ≥80%, preferably of from 95 to 80%, particularly preferably of from 90 to 80%, of the surface, in each case based on the total surface of the biological heart valve, or in particular of the heart valve leaflet, as 100%, are substantially unaltered before and after the stability-increasing treatment.

In accordance with an embodiment of the invention, the invention is characterized in that the biological material, specifically the biological heart valve, in particular the biological heart valve leaflet, based on biological material, is native biological material.

In this case, "native material" is understood to mean a biological tissue that, without extensive pre-treatment over the surface thereof, is subject substantially to just a partial stability-increasing treatment of the surface according to the invention to obtain one or more zones having increased mechanical stability. For example, it may be a biological heart valve, in particular a biological heart valve leaflet, based on biological material, characterized in that the native biological material is a collagen-based (collagen-containing) biological material.

Another preferred embodiment of the invention is characterized in that the biological material, specifically the biological heart valve and in particular the biological heart valve leaflet, based on biological material, is biological material that is a biological material already modified by a chemical pre-treatment before a partial stability-increasing treatment according to the invention of the surface to produce one or more zones having increased mechanical stability, preferably a biological material modified by decellularization. For example, this embodiment of the invention may concern a biological heart valve, in particular a biological heart valve leaflet, based on a biological material that is characterized in that the biological material already modified by chemical pre-treatment, preferably modified by decellularization, is a biological material preferably modified and/or decellularized by treatment with a 0.3 to 1.0% by weight glutaraldehyde solution based on a phosphate-buffered isotonic sodium chloride solution having a pH of from 7.2 to 7.5. More specifically, the glutaraldehyde solution or the concentration range therefore can thus be characterized, for example, as a 0.3 to 1% by weight phosphate-buffered isotonic sodium chloride solution (PBS 50 mM phosphate); a preferred pH value is the pH of 7.38.

As already discussed further above, the bioprosthetic or biological material according to the present invention is only mechanically stabilized by a separate stability-increasing treatment, in particular a separate stability-increasing chemical and/or thermal treatment, in part, that is to say is only mechanically stabilized in specific selected regions or zones. The separate stability-increasing treatment of the selected part of the surface of bioprosthetic or biological materials, in particular of bioprosthetic or biological heart valves and specifically of bioprosthetic or biological heart valve leaflets, can be implemented in a versatile manner in accordance with the present invention. For example, the separate partial treatment of the surface can be implemented by methods, with which a person skilled in the art is familiar, for treating bioprosthetic materials, specifically methods for treating biological heart valves and in particular biological heart valve leaflets. The treatment is carried out in this instance in such a way that only those regions for which an increased mechanical stability is desired are selectively subjected to a stability-increasing treatment. If native material is used, only such selected regions, for example edge regions and/or stitching regions, are accordingly preferably subject selectively in these regions to a selectively stability-increasing treatment by chemical crosslinking and/or thermal influence. If an already pre-treated biological material, specifically an already pre-treated biological heart valve and in particular an already pre-treated biological heart valve leaflet, is used, such selected regions, for example edge regions or stitching regions, can accordingly preferably be subject selectively in these regions to an additional stability-increasing treatment by chemical crosslinking and/or thermal influence. In accordance with the invention, it is thus possible to modify the surface of native or already pre-treated biological materials, specifically of native or already pre-treated biological heart valves and in particular of native or already pre-treated biological heart valve leaflets, in a locally differentiated manner as desired and to adapt said surface to the local requirements in the regions or zones treated in accordance with the invention.

The separate stability-increasing treatment according to the invention in selected regions of the surface of native or already pre-treated biological materials, specifically of native or already pre-treated biological heart valves and in particular of native or already pre-treated biological heart valve leaflets, can be implemented, by way of example but in a non-limiting manner, by the methods disclosed below in the examples. These methods are hereby also used for the production of the bioprosthetic materials according to the invention as specified hereinafter, specifically of native or of already pre-treated biological heart valves and in particular of native or of already pre-treated biological heart valve leaflets, in which the surface, due to a separate stability-increasing treatment of just part, in particular of a specific selected part, of the surface, has one or more zones having a mechanical stability that is increased compared to the mechanical stability before the stability-increasing treatment, as defined above, and wherein the properties of the remaining zones are substantially unaltered before and after the separate stability-increasing treatment.

If native material is used, only such selected regions, for example edge regions and/or stitching regions, are accordingly subject selectively in these regions to one of the separate stability-increasing treatments described hereinafter. If an already pre-treated biological material, specifically an already pre-treated biological heart valve and in particular an already pre-treated biological heart valve leaflet, is used, such selected regions, for example edge regions or stitching regions, can accordingly be subject selectively in these regions to a separate additional stability-increasing treatment. This separate or separate additional treatment may be a selective treatment of the selected regions, for example edge regions or stitching regions, by means of suitable chemical substances, such as

- a treatment with a glutaraldehyde solution, for example 0.3% by weight to 1% by weight, preferably with a 0.6% by weight phosphate-buffered isotonic sodium chloride solution (PBS 50 mM phosphate; pH 7.2-7.5; preferably pH of 7.38), of glutaraldehyde;
- a treatment with a 0.5 to 25% by weight glutaraldehyde solution in acetone, preferably with a 0.6 to 2% by weight glutaraldehyde solution in acetone;
- a treatment with chemical components, which form a polymer in situ, for example a polyurethane or a polyamide, that is to say for example a treatment with an isocyanate compound and a polyol compound to form a polyurethane or a treatment with an isocyanate compound and a polyamine compound to form a polyamide;
- a treatment with divinyl sulfone and a mixture of a branched polyethylene amine and divinyl sulfone;
- use of cyanoacrylate over the edge region; the cyanoacrylate is applied to the dried tissue, preferably on both sides, for this purpose.

The separate or separate additional treatment may also be a selective thermal treatment of the selected regions. A separate or separate additional chemical treatment may also be combined with a separate or separate additional thermal treatment if desired. The invention accordingly also relates to the embodiments of heart valves and in particular of heart valve leaflets treated in this way and detailed by way of example hereinafter.

In a first exemplary embodiment in conjunction with the separate chemical stability-increasing treatment of selected regions, for example edge regions or stitching regions, of bioprosthetic materials, the invention relates to a biological heart valve, in particular a biological heart valve leaflet, based on biological material, as described above, wherein the surface of the biological heart valve, in particular of the biological heart valve leaflet, has one or more zones having increased mechanical stability, in which the increased mechanical stability is based on a separate stability-increasing treatment of the surface of this zone or zones with a, normally aqueous, glutaraldehyde solution, preferably by treatment with a 0.3 to 1% by weight glutaraldehyde solution, particularly preferably with a 0.6% by weight glutaraldehyde solution, in the form of a phosphate-buffered isotonic sodium chloride solution (PBS 50 mM phosphate; pH 7.2-7.5, preferably pH of 7.38). The remaining zones are not treated separately or are not treated separately additionally, and the properties in these remaining zones are substantially unaltered before and after the separate stability-increasing treatment.

As an alternative to the first exemplary embodiment of the separate chemical stability-increasing treatment of selected regions of the surface and in order to produce a bioprosthetic component for an implant according to the invention, for example a biological heart valve, in particular a heart valve leaflet, based in each case on a biological material, wherein the surface of the bioprosthetic component, preferably of the biological heart valve, in particular of the heart valve leaflet, has one or more zones having increased mechanical stability, the treatment with glutaraldehyde solution can also be carried out in such a way that the increased mechanical stability is based on a separate stability-increasing treatment of the surface of these zones with a 0.5 to 25% by weight glutaraldehyde solution in acetone, preferably on a separate stability-increasing treatment with a 0.6 to 2% by weight glutaraldehyde solution in acetone.

In a second exemplary embodiment in conjunction with the separate chemical stability-increasing treatment of selected regions, for example edge regions or stitching regions, of bioprosthetic materials, the invention also relates to a biological heart valve, in particular a heart valve leaflet, based on biological material, as described above, wherein the surface of the biological heart valve, in particular of the heart valve leaflet, has one or more zones having increased mechanical stability, in which the increased mechanical stability is based on a polymer coating, which is formed in situ from a) an isocyanate component, preferably with HMDI (hexamethyldiisocyanate) as the isocyanate component; and
b) a further component selected from
b1) a polyol component, preferably with a saccharide or polysaccharide as the polyol component, if desired with addition of DABCO (1,4-diazabicyclo[2.2.2]octane) as an alkaline catalyst, or
b2) a polyamine component, preferably with polyethyleneimine as the polyamine component.

DABCO (1,4-diazabicyclo[2.2.2]octane), as an alkaline catalyst, accelerates the reaction if polyol components are used. Saccharides or polysaccharides are suitable polyol components. Polyethyleneimine is a preferred amine component. The DABCO catalyst is not required with use of polyamines.

In a third exemplary embodiment in conjunction with the separate chemical stability-increasing treatment of selected regions, for example edge regions or stitching regions, of bioprosthetic materials, the invention also relates to a biological heart valve, in particular a heart valve leaflet, based on biological material, as described above, wherein the surface of the biological heart valve, in particular of the heart valve leaflet, has one or more zones having increased mechanical stability, in which the increased mechanical stability is based on a separate stability-increasing treatment of the surface of this zone with divinyl sulfone and a mixture of a branched polyethylene amine and divinyl sulfone.

In a further exemplary embodiment in conjunction with the separate thermal stability-increasing treatment of selected regions, for example edge regions or stitching regions, of bioprosthetic materials, the invention also relates to a biological heart valve, in particular a heart valve leaflet, based on biological material, as described above, wherein the surface of the biological heart valve, in particular of the heart valve leaflet, has one or more zones having increased mechanical stability, in which the increased mechanical stability is based on a separate stability-increasing treatment of the surface of this zone by shaping and by a short-term thermal treatment, preferably with shaping by cutting with a laser and short-term thermal heating of the cut region or by shaping by punching and subsequent short-term intense heating of the punched region. Due to the heat of the laser or a warmed or heated punching die, a thermal treatment, that is to say a thermal influence, is implemented for example on the outer side of the valve, and an associated denaturing of the material in this region or in this zone is also produced.

If the biological material is punched with simultaneous heating of the edges or is first punched and then heated intensely in the short term at the edges, stabilized materials are obtained at the edges. To cut the biological material, specifically a biological heart valve, in particular a heart valve leaflet, as a result of punching together with thermal heating, the punching die scarfed on the underside is brought to a temperature of more than 75° C. The preferred temperature range for the punching operation together with thermal heating is 75-110° C., particularly preferably 80-100° C. The biological material is cut out in the predefined die. The heated punching die is generally left in contact with the tissue for a period of at least 5 sec, preferably at least 10 sec, more preferably at least 20 sec. For example, the heated punching die is left in contact with the tissue for a period of from 5 sec to 2 min, preferably 10 sec to 1 min, more preferably 20 sec to 40 sec. Alternatively to the heating of the punching die before use for punching the biological material, a heatable punching die can also be used to cut the biological material. To punch biological material, for example to punch a pericardial tissue, using a heatable punching die, a predefined heatable punching die scarfed at the underside is brought to a temperature of more than 75° C. For punching with use of a heatable punching die, said die is heated to a preferred temperature range of from 75-110° C., particularly preferably of from 80-100° C., so as to cut out the biological material by means of the heatable punching die. The heatable punching die is generally left in contact with the biological material for a period of at least 0.01 sec, preferably at least 0.1 sec, more preferably at least 1 sec. For example, the heatable punching die is left in contact with the biological material for a period of from 0.01 sec to 2 min, preferably of from 0.1 sec to 1 min, more preferably of from 1 sec to 30 sec.

When producing biological heart valve material, it has been found that the cutting with use of a laser provides better results than if the material is cut or punched mechanically. In this instance, "better results" means that the edge regions are also shaped in a more stable manner. The reason for this is the influence of the heat of the laser on the material. Biological heart valve material can thus be cut advantageously as a result of cutting with use of a laser. As a result of the laser, stabilized edge regions are advantageously formed due to the influence of the heat of the laser. Laser-cutting can be carried out using an underlying matrix, wherein the matrix is also cut at the same time if desired, or is merely used as an inert support for the biological material to be cut by the laser. Poorly thermally conducting materials are used as a matrix. Poorly thermally conducting matrix materials include plastics, preferably polyimide. Polyimides (PIs for short) are high-performance plastics of which the most important structural feature is the imide group. Further possible poorly thermally conducting plastics also include, inter alga, polybismaleinimide (PBMI), polybenzimidazole (PBI) and polyoxadiazobenzimidazol (PBO), polyimidesulfone (PISO) and polymethacrylimide (PMI). Alternatively, the matrix located beneath the biological material may also not be separated together with said biological material. In that case too, a poorly conductive, yet inert, matrix material such as glass is used. Due to a clever selection of the matrix, the amount of heat introduced by the laser can be better transferred to the tissue. The focus of the laser is adjusted so that the edge is denatured. Complete denaturing is to be avoided, however.

The invention provides bioprosthetic materials having advantageous properties, which will be explained in greater detail herein on the basis of the example of heart valves, in particular on the basis of the example of heart valve leaflets. In a heart valve, the valve leaflets experience different mechanical challenges. Similarly to artificial heart valves, biological heart valves are also surrounded by a polyester sleeve so that they can be stitched in. In accordance with the present invention, the bioprosthetic or biological material can then be prepared in a tailored manner for the respective specific use as a result of the area-defined and/or point-wise optimization of the regions of the bioprosthetic or biological material. Due to the locally defined treatment according to the invention, the bioprosthetic or biological material is adapted to the locally different stresses. The bioprosthetic or biological material thus produced can be better stitched for example. Due to the stitching region reinforced selectively in accordance with the invention, yarns no longer rip out. The entire heart valve can be crimped more easily over a smaller radius. The pericardium of the heart valve treated in accordance with the invention is softer over its surface and only the edges are crosslinked and thus stiffer. Pressure points no longer occur. The bioprosthetic or biological material is elastic, impressions caused by the crimping process reform more easily, and previously damaged points, at which the bioprosthetic or biological material could fail, no longer occur. For clinical use, the actual heart valve tissue is used fastened on a stent or without a stent.

As a result of the invention a contribution is thus made to increased usability of biological heart valves, in particular biological heart valve leaflets. As a result of the present invention, stability of the heart valve leaflet is improved without chemically or thermally altering the entire bioprosthetic or biological material. Merely the regions in which tears or material weakness have been found to occur in accordance with experience are preferably stabilized additionally. As a result of the reinforcement of the biological heart valve according to the invention at the expedient points, the majority of the surface remains chemically or thermally uninfluenced and is therefore more compatible with the body. A further advantage of the present invention lies in the fact that the biological material can be adapted accordingly to the requirements. The edges, at which the material is to be stitched to the frame or stent, can thus be reinforced specifically so as to achieve a particularly high level of suture retention.

The invention accordingly also relates to bioprosthetic materials having improved material properties, in particular such as improved tear resistance and/or the material characteristics already defined, as disclosed above.

The invention therefore also relates to a biological heart valve, in particular a heart valve leaflet, based on biological material, as described above, wherein the biological heart valve, in particular the heart valve leaflet, has one of the following material properties (for example tear resistance): a) SRS of from 30 to 450 N/mm$^2$, preferably of from 50 to 300 N/mm$^2$; b) SRS more preferably of from 100 to 200 N/mm$^2$, more preferably of from 150 to 200 N/mm$^2$.

The preferred bioprosthetic materials according to the invention, specifically the biological heart valves and in particular the biological heart valve leaflets, can be obtained by a separate treatment of specific selected parts of the surface, as already illustrated in conjunction with the description of said materials. The invention therefore also relates to a method for producing a biological heart valve, in particular a biological heart valve leaflet, as described and defined above, wherein the biological heart valve, in particular the biological heart valve leaflet, is based on a natural or possibly already modified biological material and of which the surface has one or more zones having an increased mechanical stability, and is characterized in that just one (selected) part of the surface of the biological heart valve, in particular of the biological heart valve leaflet, is subjected to a separate stability-increasing treatment, preferably a separate stability-increasing chemical and/or thermal treatment, so as to produce one or more zones having a mechanical stability that is increased compared to the mechanical stability before the stability-increasing treatment, and wherein, in each case based on the total surface of the biological heart valve, or in particular of the heart valve leaflet, as 100%, the zones with increased mechanical stability are formed by a maximum proportion of up to 40% of the surface and the properties of the remaining zones having a proportion of at least 60% of the surface are substantially unaltered by the stability-increasing treatment.

EXAMPLES

For modern biological heart valve leaflets, decellularization is imperative. Methods for decellurization are known sufficiently by a person skilled in the art. Chemical crosslinking by means of glutaraldehyde is likewise an introduced, tried and tested method. By contrast, the present invention describes (area-based) partial, possibly only additional, chemical crosslinking of the biological heart valve leaflet using glutaraldehyde. Furthermore, further chemical methods for (area-based) partial, possibly only additional, chemical or thermal crosslinking of the biological heart valve leaflet are given as examples. The biological materials of the present invention are characterized by mechanical differences between the edge region and the remaining area of the biological material. In this case a biological material that is already fully crosslinked and fixed as in the prior art, for example a tissue that is initially fully crosslinked and fixed similarly to example 1, can also be used, wherein, in accordance with the present invention, the edge region for example or any other desired region of the biological material still undergoes a separate additional treatment according to the invention however.

Unless stated otherwise, the percentages given in the following examples are percentages by weight.

Practical Example 1

Chemical Crosslinking of the Edge Region of a Biological Material

In the event of chemical crosslinking of the edge region of a biological material, wherein pericardium or the heart sac can be named as an example of a commonly used biological material, although any other connective tissue containing collagen may also be used, only the desired regions are dipped into a crosslinking solution. For partial chemical crosslinking of a biological heart valve leaflet by means of glutaraldehyde, a 0.6% by weight glutaraldehyde solution is prepared, into which merely the edge region of the biological heart valve leaflet is dipped. After 10 min exposure time, the material is freed of adhering crosslinking agent (glutaraldehyde solution; phosphate-buffered isotonic sodium chloride solution; PBS 50 mM phosphate; pH 7.2-7.5) by blotting off or evaporation of the crosslinking solvent (acetone), and is introduced into a heat cupboard and incubated for 1 h at 50° C. This process can be repeated.

Practical Example 2

Coating of the Edge Region

The biological materials of the present invention are characterized by mechanical differences between the edge region and the remaining area of the biological material. In the present example, a fully crosslinked and fixed biological material, that is to say in this case a heart valve leaflet, and thereafter the edge region are subjected to a separate additional treatment according to the invention to achieve this difference.

For chemical crosslinking and fixing of the aforesaid biological heart valve leaflet, the entire pericardium piece is initially placed in a cold (4° C.) 0.6% glutaraldehyde solution and is incubated in a cold cupboard for 12 hrs. The glutaraldehyde crosslinking solution is then changed and the pericardium piece is crosslinked further at 21° C. (room temperature) for 48 hrs. For the additional (area-based) partial chemical crosslinking according to the invention of the entire pre-treated (crosslinked and fixed) biological heart valve leaflet, an isocyanate component is then sprayed merely over the edge region. HMDI is suitable in this instance. After incubation for 10 min at 40° C., a mixture of HMDI and polyol component or polyamine component is then applied to this first layer of the isocyanate component. DABCO, as an alkaline catalyst, accelerates the reaction. Saccharides or polysaccharides are suitable polyol components. Polyethyleneimine is a suitable amine component. DABCO is not required with use of polyamines.

Practical Example 3

Stabilization of the Edge Region by Treatment with Divinyl Sulfone and a Mixture of a Branched Polyethyleneimine and Divinyl Sulfone The addition of 0.1% KOH accelerates the crosslinking reaction for the material from example 2. Divinyl sulfone is used in the form of 1 to 11% aqueous solution. A 5-10% solution is preferable. The edge regions are dipped into this solution for 15 min and then removed. Alternatively, the edge region can also be sprayed with a 10% DVS/water solution. If 0.1% KOH is added, the solution has to be cooled over ice. After the spraying process, the tissue is heated to 40° C. for 30 min.

After this treatment, the material is already stabilized at the edge. A further treatment with polyethyleneimine leads to a further stabilization, as is expedient in particular for the stitching region. To this end, the tissue is dipped in polyethyleneimine after the initial dipping or spraying process. Once removed and blotted off, the tissue is incubated for 30 min at 40° C.

Practical Example 4

Punching of Pericardial Tissue Using a Preheated Die

The die scarfed on the underside is pre-heated to a temperature above 88° C. The pericardium from pig, cow or horse is cut out in the predefined punching die. Any other connective tissue containing collagen can also be processed in this manner. The pre-heated die is left in contact with the tissue for 40 sec. Due to the pre-heated die, a thermal treatment is implemented on the outer side of the valve, and an associated denaturing of the biological material, that is to say in this example of the pericardial tissue, is also produced. This heat-induced protein folding is very beneficial for the mechanical properties.

Practical Example 5

Punching of the Pericardial Tissue Using a Heatable Die

The die scarfed on the underside is heated to a temperature above 88° C. The pericardium from example 4 is cut out in the predefined die. The heatable punching die heated to the predefined temperature is left in contact with the tissue for a period of 30 sec. Due to the heated punching die, a thermal treatment is implemented on the outer side of the valve, and an associated denaturing of the material is also produced. This heat-induced protein folding is very beneficial for the mechanical properties.

Practical Example 6

Biological heart valve material may advantageously be cut with use of a suitable laser, known to a person skilled in the art. As a result of the laser, stabilized edge regions are advantageously formed due to the influence of the heat of the laser. Laser-cutting can be carried out using an underlying matrix, wherein the matrix is also cut at the same time if desired, or is merely used as an inert support for the biological material to be cut by the laser. The laser-cutting of the biological tissue is preferably carried out with an underlying matrix, which is cut together with the tissue and consists of a poorly thermally conducting material. Poorly thermally conducting matrix materials include plastics, preferably polyimide. Polyimides (PIs for short) are high-performance plastics of which the most important structural feature is the imide group. These include, inter alia, polybismaleinimide (PBMI), polybenzimidazole (PBI) and polyoxadiazobenzimidazol (PBO), polyimidesulfone (PISO) and polymethacrylimide (PMI).

Alternatively, the matrix may also not be separated together with the biological material. In that case too, a poorly conductive matrix material such as glass is used. Due to a clever selection of the matrix, the amount of heat introduced by the laser can be better transferred to the tissue. The focus of the laser is adjusted so that the edge is denatured. Complete denaturing is to be avoided, however.

Practical Example 7

The crosslinked tissue from Example 2 is provided with a seam at the edge region. The edge is stitched using a suitable yarn. Different sewing techniques are known from the textiles industry and can be used. A monofilament or a multifilament can be used as suture material. For example, TEVDEK II® by Deknatel or PROFILEN® by Lenzing. Pure Teflon has proven to be particularly expedient due to its low coefficient of friction during the sewing process.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A biosprosthetic component for a circulatory system implant comprising a surface of a biological material with one or more zones having increased mechanical stability compared to a remaining zone, wherein the increased mechanical stability is from shaping and by a short-term thermal treatment, further wherein the one or more zones having increased mechanical stability account for a proportion of at least 2% and up to 40% of the surface.

2. The biosprosthetic component of claim 1, wherein the biological material is punched with simultaneous heating at edges.

3. The biosprosthetic component of claim 1, wherein the biological material is punched then heated.

4. The biosprosthetic component of claim 1, wherein the biological material is laser cut.

5. The biosprosthetic component of claim 1, wherein the bioprosthetic component is a heart valve leaflet.

6. The biosprosthetic component of claim 1, wherein the biological material is decellularized.

7. The biosprosthetic component of claim 1, wherein the one or more zones having increased mechanical stability have a suture retention strength (SRS) from 30 to 450 N/mm$^2$.

8. The biosprosthetic component of claim 1, wherein at least 10% of the surface has the increased mechanical stability.

9. The biosprosthetic component of claim 8, wherein 10% to 20% of the surface has the increased mechanical stability.

10. The bioprosthetic component of claim 1, wherein the biological material is modified by treatment with a 0.3 to 1.0% by weight glutaraldehyde solution based on a phosphate-buffered isotonic sodium chloride solution having a pH of from 7.2 to 7.5.

11. The biosprosthetic component of claim 1, wherein the implant is selected from the group consisting of a mitral heart valve, an aortic heart valve, a pulmonary heart valve, and a venous valve.

12. A bioprosthetic component for a circulatory system implant comprising a surface of a biological material with one or more zones having increased mechanical stability compared to a remaining zone, wherein the increased mechanical stability is from shaping and by a short-term thermal treatment, further wherein the one or more zones having increased mechanical stability account for a proportion up to 40% of the surface, further wherein the one or more zones having increased mechanical stability have a suture retention strength (SRS) from 30 to 450 N/mm².

13. The biosprosthetic component of claim 12, wherein the bioprosthetic component is a heart valve leaflet.

14. The biosprosthetic component of claim 12, wherein the implant is selected from the group consisting of a mitral heart valve, an aortic heart valve, a pulmonary heart valve, and a venous valve.

15. The biosprosthetic component of claim 12, wherein at least 10% of the surface has the increased mechanical stability.

16. The biosprosthetic component of claim 12, wherein the biological material is punched with simultaneous heating at edges.

17. The biosprosthetic component of claim 12, wherein the biological material is punched then heated.

18. The biosprosthetic component of claim 12, wherein the biological material is laser cut.

19. The biosprosthetic component of claim 12, wherein the biological material is decellularized.

20. The bioprosthetic component of claim 12, wherein the biological material is modified by treatment with a 0.3 to 1.0% by weight glutaraldehyde solution based on a phosphate-buffered isotonic sodium chloride solution having a pH of from 7.2 to 7.5.

* * * * *